US005436390A

United States Patent [19]
Oestreich

[11] Patent Number: 5,436,390
[45] Date of Patent: Jul. 25, 1995

[54] INBRED CORN LINE PHR03

[75] Inventor: Dean C. Oestreich, Ankeny, Iowa

[73] Assignee: Pioneer Hi-Bred International, Inc., Des Moines, Iowa

[21] Appl. No.: 166,809

[22] Filed: Dec. 13, 1993

Related U.S. Application Data

[63] Continuation of Ser. No. 649,795, Feb. 1, 1991, abandoned.

[51] Int. Cl.$^6$ .......................... A01H 5/00; A01H 4/00; A01H 1/00; C12N 5/04
[52] U.S. Cl. .................................... 800/200; 800/250; 800/DIG. 56; 435/240.4; 435/240.49; 435/240.5; 47/58
[58] Field of Search ............... 800/200, DIG. 56, 250; 47/58.03, 58.05; 435/240.4, 240.49, 240.5

[56] References Cited

PUBLICATIONS

Hallauer et al., (1988), Corn & Corn Improvement, pp. 463–564, ASA Publication #18, 3rd edition.

Poehlman, (1987), "Breeding Field Crops", AVI Publishing Co., pp. 237–246.

Troyer et al., Crop Science, vol. 25, (1985), pp. 2695–2697.

Meghji et al., Crop Science, vol. 24, (1986), pp. 545–549.

Phillips et al., Corn & Corn Improvement, ASA Monograph #18, 3rd edition, G. F. Sprogue editor, pp. 345–349 & 356–357, (1988).

Sass, (1977), Corn & Corn Improvement, ASA Monograph #18, 2nd edition, Editor G. F. Sprogue, pp. 89–110.

Primary Examiner—Gary Benzion
Attorney, Agent, or Firm—Pioneer Hi-Bred International, Inc.

[57] ABSTRACT

According to the invention, there is provided an inbred corn line, designated PHR03. This invention thus relates to the plants and seeds of inbred corn line PHR03 and to methods for producing a corn plant produced by crossing the inbred line PHR03 with itself or with another corn plant. This invention further relates to hybrid corn seeds and plants produced by crossing the inbred line PHR03 with another corn line or plant.

6 Claims, No Drawings

INBRED CORN LINE PHR03

CROSS REFERENCE TO RELATED APPLICATION

This is a continuation of prior application No. 07/649,795, filed Feb. 1, 1991, now abandoned.

FIELD OF THE INVENTION

This invention is in the field of corn breeding, specifically relating to an inbred corn line designated PHR03.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (*Zea mays L.*) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs ($A \times B$ and $C \times D$) and then the two $F_1$ hybrids are crossed again ($A \times B) \times (C \times D$). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

SUMMARY OF THE INVENTION

According to the invention, there is provided a novel inbred corn line, designated PHR03. This invention thus relates to the seeds of inbred corn line PHR03, to the plants of inbred corn line PHR03, and to methods for producing a corn plant produced by crossing the inbred line PHR03 with itself or another corn line. This invention further relates to hybrid corn seeds and plants produced by crossing the inbred line PHR03 with another corn line.

DEFINITIONS

In the description and examples that follow, a number of terms are used herein. In order to provide a clear and consistent understanding of the specification and claims, including the scope to be given such terms, the following definitions are provided:

BAR PLT=BARREN PLANTS. This is the percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the mean for the experiments in which the inbred or hybrid was grown.

DRP EAR=DROPPED EARS. This is a measure of the number of dropped ears per plot and represents the percentage of plants that did not drop ears prior to harvest.

EAR HT=EAR HEIGHT. The ear height is a measure from the ground to the top developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barget Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete. % MN is percent of the mean for the experiments in which the inbred or hybrid was grown.

PRM=PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT UNADJUSTED. The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV=Maize Dwarf Mosaic Virus & MCDV=Maize Chlorotic Dwarf Virus): Visual rating (1-9 score) where a "1" is very susceptible and a "9" is very resistant.

SLF BLT=Southern Leaf Blight (*Bipolaris maydis, Helminthosporium maydis*): Visual rating (1-9 score) where a "1" is very susceptible and a "9" is very resistant.

NLF BLT=Northern Leaf Blight (*Exserohilum turcicum, H. turcicum*): Visual rating (1-9 score) where a "1" is very susceptible and a "9" is very resistant.

COM RST=Common Rust (*Puccinia sorghi*): Visual rating (1-9 score) where a "1" is very susceptible and a "9" is very resistant.

GLF SPT=Gray Leaf Spot (*Cercospora zeae-maydis*): Visual rating (1-9 score) where a "1" is very susceptible and a "9" is very resistant.

STW WLT=Stewart's Wilt (*Erwinia stewartii*): Visual rating (1-9 score) where a "1" is very susceptible and a "9" is very resistant.

HD SMT=Head Smut (*Spacelotheca reiliana*): Percentage of plants that did not have infection.

EAR MLD=General Ear Mold: Visual rating (1-9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1-9 score) of post flowering damage due to infestation by European Corn Borer. A "1" is very susceptible and a "9" is very resistant.

ECB 1LF=European Corn Borer First Brood (*Ostrinia nubilalis*): Visual rating (1-9 score) of pre-flowering leaf feeding by European Corn Borer. A "1" is very susceptible and a "9" is very resistant.

DETAILED DESCRIPTION OF THE INVENTION

Inbred corn line PHR03 is a yellow, dent corn inbred that is best suited as a male in crosses for producing first generation F1 corn hybrids. PHR03 is best adapted to the Eastern part of the United States, but also does well in Western regions with its Northern boundary being about Des Moines, Iowa. The inbred can be used to produce hybrids from approximately 117-130 relative maturity based on the Minnesota Relative Maturity Rating System for harvest moisture of grain. PHR03 should make a very good male as it has very good vigor, stand establishment, and very large tassels. The inbred in hybrid combination has excellent yield, overall good grain appearance, and below average root lodging.

The inbred has shown uniformity and stability within the limits of environmental influence for all the traits as described in the Variety Description Information (Table 1) that follows. Most of the data in the Variety Description information was collected at Johnston, Iowa. The inbred has been self-pollinated and ear-rowed a sufficient number of generations with careful attention paid to uniformity of plant type to ensure homozygousity and phenotypic stability. The line has been increased both by hand and in isolated fields with continued observation for uniformity. No variant traits have been observed or are expected in PHR03.

Inbred corn line PHR03, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PHR03

Type: Dent     Region Best Adapted: Most Regions

A. Maturity: Average across maturity zones. Zone: 0
    Heat Unit Shed:    1550
    Heat Unit Silk:     1590
    No. Reps:          76

HEAT UNITS =

$$\frac{[\text{Max. Temp. } (<\_86° \text{ F.}) + \text{Min. Temp. } (>\_50° \text{ F.})]^*}{2} - 50$$

B. Plant Characteristics:
    Plant height (to tassel tip): 246 cm
    Length of top ear internode: 11 cm
    Number of ears per stalk: Single
    Ear height (to base of top ear): 85 cm
    Number of tillers: None
    Cytoplasm type: Normal C. Leaf:
    Color: Dark Green (B14)
    Angle from Stalk: <30 degrees
    marginal Waves: Few (WF9)
    Number of Leaves (mature plants): 19
    Sheath Pubescence: Light (W22)
    Longitudinal Creases: Few (OH56A)
    Length (Ear node leaf): 79 cm
    Width (widest point, ear node leaf): 9 cm D. Tassel:
    Number lateral branches: 10
    Branch Angle from central spike: 30-40 degrees
    Pollen Shed: Heavy based on Pollen Yield Test
    (139 % of experiment means)
    Peduncle Length (top leaf to basal branches): 19 cm
    Anther Color: Yellow
    Glume Color: Green E. Ear (Husked Ear Data Except When Stated otherwise):
    Length: 19 cm
    Weight: 117 gm
    Mid-point Diameter: 40 mm
    Silk Color: Pink
    Husk Extension (Harvest stage): Medium (Barely covering ear)

TABLE 1-continued
VARIETY DESCRIPTION INFORMATION
INBRED = PHR03

Type: Dent      Region Best Adapted: Most Regions

- Husk Leaf: Short (<8 cm)
- Taper of Ear: Slight
- Position of Shank (dry husks): Pendent
- Kernel Rows: Straight, Distinct Number = 16
- Husk Color (fresh): Light Green
- Husk Color (dry): Buff
- Shank Length: 15 cm
- Shank (No. of internodes): 9

F. Kernel (Dried):
   Size (from ear mid-point)
   - Length: 10 mm
   - Width: 8 mm
   - Thick: 5 mm
   - Shape Grade (% rounds): 40–60 (46 % medium round based on Parent Test Data)
   - Pericarp Color: Colorless
   - Aleurone Color: Homozygous Yellow
   - Endosperm Color: Yellow
   - Endosperm Type: Normal Starch
   - Gm Wt/100 Seeds (unsized): 24 gm G. Cob:
   - Diameter at mid-point: 25 mm
   - Strength: Strong
   - Color: Red H. Diseases:
   - Corn Lethal Necrosis (MCMV = Maize Chlorotic Mottle Virus and MDMV = Maize Dwarf Mosaic Virus): Intermediate Maize Dwarf mosaic Complex (MDMV & MCDV-Maize Dwarf Virus): Susceptible
   - Anthracnose Stalk Rot (*C. graminicola*): Intermediate
   - S. Leaf Blight (*B. maydis*) : Intermediate
   - N. Leaf Blight (*E. turcicum*): Intermediate
   - Common Rust (*P. sorghi*): Resistant
   - Southern Rust (*P. polysora*): Intermediate
   - Gray Leaf Spot (*C. zeae*): Intermediate
   - Stewart's Wilt (*E. stewartii*): Resistant
   - Goss's Wilt (*C. nebraskense*): Highly Resistant
   - Fusarium Ear Mold (*F. moniliforme*): Resistant I. Insects:
   - European Corn Borer-1 Leaf Damage (Pre-flowering): Intermediate
   - European Corn Borer-2 (Post-flowering): Intermediate
   - The above descriptions are based on a scale of 1–9, 1 being highly susceptible, 9 being highly resistant.
   - S (Susceptible): Would generally represent a score of 1–3.
   - I (Intermediate): Would generally represent a score of 4–5.
   - R (Resistant): Would generally represent a score of 6–7.
   - H (Highly Resistant): would generally represent a score of 8–9. Highly resistant does not imply the inbred is immune.

J. Variety Most Closely Resembling:
   | Character | Inbred |
   |---|---|
   | Maturity | PHG84 |
   | Usage | PHG84 |

*If maximum is greater than 86 degrees fahrenheit, then 86 is used and if minimum is less than 50, then 50 is used. Heat units accumulated daily and can not be less than 0.

PHG84 (PVP Certificate No. 8300130) are Pioneer Hi-Bred International, Inc. proprietary inbred.

Data for Items B, C, D, E, F, and G are based primarily on a maximum of six reps from Johnston, Iowa grown in 1988 and 1989, plus description information from the maintaining station.

ELECTROPHORESIS RESULTS
Isozyme Genotypes for PHR03

Isozyme data were generated for inbred corn line PHR03 according to the procedures described in Stuber, C. W., Wendel, J. F., Goodman, M. M., and Smith, J. S. C., "Techniques and Scoring Procedures for Starch Gel Electrophoresis of Enzymes from Maize (*Zea mays L.*)", *Technical Bulletin No. 286, North Carolina Agricultural Research Service*, North Carolina State University, Raleigh, N.C. (1988).

The data in Table 2 compares PHR03 with its parents, PHT19 and PHG84.

TABLE 2
ELECTROPHORESIS RESULTS FOR PHR03 AND ITS PARENTS PHT19 AND PHG84

| LOCI | PHR03 | PARENTS PHT19 | PHG84 |
|---|---|---|---|
| ACP1 | 4 | 4 | 4 |
| ADH1 | 4 | 4 | 4 |
| CAT3 | 9 | 9 | 9 |
| DIA1 | 8 | 8 | 8 |
| GOT1 | 4 | 4 | 4 |
| GOT2 | 4 | 4 | 4 |
| GOT3 | 4 | 4 | 4 |
| IDH1 | 4 | 4 | 4 |
| IDH2 | 6 | 4 | 6 |
| MDH1 | 6 | 6 | 6 |
| MDH2 | 3.5 | 6 | 3.5 |
| MDH3 | 16 | 16 | 16 |
| MDH4 | 12 | 12 | 12 |
| MDH5 | 12 | 12 | 12 |
| MMM | 4 | 4 | 4 |
| PGM1 | 9 | 9 | 9 |
| PGM2 | 3 | 8 | 3 |
| PGD1 | 3.8 | 3.8 | 2 |
| PGD2 | 5 | 5 | 5 |
| PHI1 | 4 | 4 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHR03. Further, both first and second parent corn plants can come from the inbred corn line PHR03. Thus, any such methods using the inbred corn line PHR03 are part of this invention: selfing, backcrosses, hybrid production, crosses to populations, and the like. All plants produced using inbred corn line PHR03 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottsville, Va. 1982, at 367–372) and in Duncan, et al., "The Production of Callus Capable of Plant Regeneration from Immature Embryos of Numerous Zea Mays Genotypes," 165 *Planta* 322–332 (1985). Thus, another aspect of this invention is to provide cells which upon growth and differentiation produce the inbred line PHR03.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHR03, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE 3

Inbred and Hybrid Performance of PHR03

In the examples that follow, the traits and characteristics of inbred corn line PHR03 are given as a line and in hybrid combination. The data collected on inbred corn line PHR03 is presented for the key characteristics and traits.

The results in Table 3A compare PHR03 to its PHT19 parent. The results show PHR03 has higher yield and grain harvest moisture and significantly higher test weight than PHT19. PHR03 is taller with higher ear placement and flowers (GDU Shed and GDU Silk) later than PHT19. PHR03 has better grain appearance and significantly better stay green than PHT19.

Table 3B compares PHR03 to its other parent, PHG84. PHR03 has significantly higher yield, higher moisture at grain harvest, and higher test weight than PHG84. PHR03 is a taller plant with higher ear placement and flowers (GDU Shed and GDU Silk) earlier than PHG84. PHR03 has significantly better seedling vigor and early stand than PHG84. The pollen weight is greater and grain appearance is better for PHR03 compared to PHG84. The agronomic and disease scores for PHR03 compared to PHG84 are similar except PHR03 has slightly poorer stalks.

Tables 3C through 3F compare PHR03 with other Pioneer proprietary inbreds with similar genetic backgrounds, similar usage and proven performance in the area where PHR03 is adapted.

The results in Table 3C show PHR03 is higher yielding, has similar grain harvest moisture, and slightly lower test weight compared to PHM49. PHR03 is taller with higher ear placement and flowers (GDU Shed and GDU Silk) later than PHM49. PHR03 has larger ears, fewer barren plants, and significantly better seedling vigor and early stand establishment than PHM49. PHR03 has significantly higher pollen weight and is less susceptible to tassel blast than PHM49. PHR03 has significantly lower stay green and slightly more resistance to stalk lodging, and has slightly better root lodging resistance than PHM49. PHR03 has better ear mold, Northern leaf blight, Southern leaf blight, and first brood European corn borer resistance, but is slightly more susceptible to Southern rust and second brood European corn borer than PHM49.

PHR03 is lower yielding, higher in grain harvest moisture, and has similar test weight compared to PHN46 (Table 3D). PHR03 is a significantly taller inbred with higher ear placement and flowers (GDU Shed and GDU Silk) significantly later than PHN46. PHR03 has larger ear size but more barren plants than PHN46. The pollen weight of PHR03 is significantly greater and has larger tassels than PHN46. Grain appearance in PHR03 is slightly worse but has better stay green than PHN46. In the area of disease and insect resistance, PHR03 has slightly overall better resistance than PHN46.

The results in Table 3E show PHR03 has lower yield and moisture at grain harvest than PHR63. PHR03 is a significantly taller inbred with higher ear placement and flowers (GDU Shed and GDU Silk) significantly later than PHR63. PHR03 has significantly larger ears and greater pollen weight than PHR63. PHR03 is more susceptible to first brood European corn borer, but shows more resistance to grey leaf spot and second brood European corn borer than PHR63.

The results in Table 3F show PHR03 has higher yield, grain harvest moisture, and test weight than PHV78. PHR03 is significantly shorter and flowers (GDU Shed and GDU Silk) slightly earlier than PHV78. PHR03 has fewer barren plants, better seedling vigor, and significantly higher early stand count than PHV78. The ear size of PHR03 is larger, but pollen weight is less and tassel size smaller than PHV78. PHR03 has significantly better grain appearance and resistance to root lodging but is more susceptible to stalk lodging than PHV78. PHR03 is more resistant to ear mold, grey leaf spot and Southern leaf blight, but more susceptible to head smut and first brood European corn borer than PHV78.

The results in Table 4A compare PHR03 to PHJ90 crossed to the same inbred testers. In this comparison, PHR03 hybrids yield more, have higher grain harvest moisture, and have slightly higher test weight than PHJ90 hybrids. The PHR03 hybrids are taller with higher ear placement and flower (GDU Shed) later than PHJ90 hybrids. PHR03 hybrids have better stalk lodging resistance, stay green, and grain appearance than PHJ90 hybrids.

Table 4B compares PHR03 to PHK56 crossed to the same inbred testers. The results show PHR03 hybrids are higher yielding, have higher grain moisture, and have slightly higher test weight than PHK56 hybrids. The PHR03 hybrids are slightly taller with higher ear placement and flower (GDU Shed) later than PHK56 hybrids. The PHR03 hybrids have better stalk lodging resistance, stay green, grain appearance, seedling vigor, and early stand count, but are more susceptible to root lodging than PHK56 hybrids.

The results in Table 4C compare PHR03 to PHM49 crossed to the same inbred testers. In this comparison, the PHR03 hybrids yield more and have slightly higher grain harvest moisture and test weight than PHM49 hybrids. Compared to the PHM49 hybrids, the PHR03 hybrids are taller and have higher ear placement plus flower (GDU Shed) slightly later. The PHR03 hybrids have better grain appearance, better seedling vigor, higher early stand count, and fewer brittle stalks, but lower stay green than PHM49 hybrids.

The results in Table 4D compare PHR03 to PHN46 crossed to the same inbred testers. In this comparison, PHR03 hybrids yield more, have more grain moisture at maturity, and have higher test weight than PHN46 hybrids. PHR03 hybrids are taller with higher ear placement and flower (GDU Shed) slightly later than PHN46 hybrids. PHR03 hybrids have better grain appearance and fewer brittle stalks, but have poorer stay green than PHN46 hybrids.

Results in Table 4E compare PHR03 to PHR55 crossed to the same inbred testers. The PHR03 hybrids are higher yielding, have less grain harvest moisture, and have higher test weight than PHR55 hybrids. The PHR03 hybrids are slightly taller with higher ear placement compared to the PHR55 hybrids. PHR03 hybrids have slightly better stalk lodging resistance and stay green and fewer brittle stalks, but are more susceptible to root lodging than PHR55 hybrids.

The results in Table 4F compare PHR03 to PHR63 crossed to the same inbred testers. PHR03 hybrids are higher yielding, have lower grain harvest moisture, and have slightly higher test weight than PHR63 hybrids. The PHR03 hybrids are taller and flower (GDU Shed) later than PHR63 hybrids. PHR03 hybrids have better stalk lodging resistance, stay green, grain appearance, and fewer brittle stalks, but have poorer seedling vigor and are more susceptible to root lodging than PHR63 hybrids.

Table 4G compares PHR03 to PHT22 crossed to the same inbred testers. The data shows PHR03 hybrids have higher yielding, higher grain harvest moisture, and higher test weight than PHT22 hybrids. PHR03 hybrids are slightly taller, but ear placement is lower than PHT22 hybrids. PHR03 hybrids have better root lodging resistance and stay green, but are more susceptible to stalk lodging than PHT22 hybrids.

Tables 5 through 12 compare PHR03 hybrids to Pioneer Brand Hybrids 3503, 3417, 3398, 3317, 3189, 3180, 3162, and 3159, respectively. Each hybrid has a parent in common with a PHR03 hybrid other than PHR03. The hybrids are adapted to much of the same area as the PHR03 hybrids. Table 5 compares a PHR03 hybrid with 3503. The data shows the PHR03 hybrid is higher yielding and has higher grain harvest moisture with similar test weight compared to 3503. The PHR03 hybrid is taller with higher ear placement and flowers (GDU Shed) later than 3503. Compared to 3503, the PHR03 hybrid has better grain appearance, stay green, and stalk lodging resistance, but is more susceptible to root lodging.

Table 6 compares a PHR03 hybrid to Pioneer Brand Hybrid 3417. The PHR03 hybrid has higher yield, grain harvest moisture, and test weight than 3417. The results show the PHR03 hybrid is taller with higher ear placement and flowers (GDU Shed) later than 3417. The PHR03 hybrid has better grain appearance, stay green, stalk lodging resistance, and fewer brittle stalks, but is more susceptible to root lodging than 3417.

The results in Table 7, comparing a PHR03 hybrid to Pioneer Brand Hybrid 3398, show the PHR03 hybrid is higher yielding, has higher grain harvest moisture, and has higher test weight than 3398. The PHR03 hybrid is taller with higher ear placement and flowers (GDU Shed) later than 3398. The PHR03 hybrid has better grain appearance, stay green, stalk lodging resistance, and fewer brittle stalks compared to 3398.

Table 8 compares a PHR03 hybrid to Pioneer Brand Hybrid 3317. The PHR03 hybrid is higher yielding, has slightly higher grain harvest moisture, and has significantly better test weight than 3317. The PHR03 hybrid is taller with higher ear placement and flowers (GDU Shed) later than 3317. The PHR03 hybrid has better grain appearance and fewer brittle stalks, but has poorer seedling vigor and lower early stand count plus is more susceptible to stalk and root lodging compared to 3317.

Table 9 compares a PHR03 hybrid to Pioneer Brand Hybrid 3189. The PHR03 hybrid is higher yielding, has lower grain harvest moisture, and has significantly better test weight than 3189. The PHR03 hybrid is significantly taller with higher ear placement and flowers (GDU Shed) later than 3189. The PHR03 hybrid has better seedling vigor and higher early stand count than 3189. The results show the PHR03 hybrid has better grain appearance and fewer brittle stalks, but has worse stay green and is more susceptible to stalk and root lodging than 3189.

The results in Table 10 compare a PHR03 hybrid to Pioneer Brand Hybrid 3180. The PHR03 hybrid is higher yielding, has similar grain harvest moisture, and test weight is greater compared to 3180. The PHR03 hybrid is taller, but ear height and flowering (GDU Shed) are similar compared to 3180. The results show the PHR03 hybrid has better grain appearance, is more resistant to root lodging, and has fewer brittle stalks than 3180.

Table 11 compares a PHR03 hybrid to Pioneer Brand Hybrid 3162. The PHR03 hybrid has higher yield and test weight and lower grain harvest moisture than 3162. The PHR03 hybrid is taller with higher ear placement and flowers (GDU Shed) later than 3162. The PHR03 hybrid has better stalk lodging resistance and fewer brittle stalks compared to 3162.

Table 12 compares a PHR03 hybrid to Pioneer Brand Hybrid 3159. The PHR03 hybrid has higher yield and test weight, but lower grain harvest moisture than 3159. The PHR03 hybrid is significantly taller with higher ear placement and flowers (GDU Shed) later than 3159. Seedling vigor is better and stand count is greater for the PHR03 hybrid compared to 3159. The PHR03 hybrid has poorer stay green and is slightly more susceptible to root lodging, but has slightly better stalk lodging and fewer brittle stalks than 3159.

TABLE 3A

PAIRED INBRED COMPARISON DATA
VARIETY #1 = PHR03
VARIETY #2 = 2 PHT19

|  | VAR # | BU ACR ABS | BU ACR % MN | MST ABS | BAR PLT ABS | PLT HT ABS | EAR HT ABS | SDG VGR ABS | EST CNT ABS | DRP EAR ABS |
|---|---|---|---|---|---|---|---|---|---|---|
| TOTAL SUM | 1 | 72.8 | 149 | 22.5 | 94.9 | 97.0 | 34.5 | 4.0 | 46.2 | 100.0 |
|  | 2 | 66.9 | 137 | 15.8 | 95.0 | 91.5 | 30.0 | 4.3 | 47.8 | 99.6 |

TABLE 3A-continued

PAIRED INBRED COMPARISON DATA
VARIETY #1 = PHR03
VARIETY #2 = 2 PHT19

|  | LOCS | 3 | 3 | 3 | 3 | 2 | 2 | 3 | 3 | 3 |
|---|---|---|---|---|---|---|---|---|---|---|
|  | DIFF | 5.9 | 12 | 6.7 | 0.1 | 5.5 | 4.5 | 0.3 | 1.7 | 0.4 |
|  | PROB | .126 | .134 | .070* | .951 | .437 | .139 | .184 | .109 | .423 |

|  | TIL LER ABS | GDU SHD ABS | GDU SLK ABS | POL SC ABS | TST WT ABS | GRN APP ABS | STA GRN ABS | STK LDG ABS | RT LDG ABS |
|---|---|---|---|---|---|---|---|---|---|
| TOTAL SUM | 1.2 | 1570 | 1580 |  | 56.8 | 6.3 | 6.3 | 82.6 | 100.0 |
|  | 1.5 | 1480 | 1470 |  | 51.6 | 5.0 | 2.8 | 79.6 | 99.2 |
|  | 3 | 1 | 1 |  | 3 | 3 | 3 | 3 | 3 |
|  | 0.3 | 90 | 110 |  | 5.1 | 1.3 | 3.5 | 3.0 | 0.8 |
|  | .842 |  |  |  | .028+ | .270 | .000# | .740 | .423 |

\* = 10% SIG  
\+ = 5% SIG  
\# = 1% SIG

TABLE 3B

PAIRED INBRED COMPARISON DATA
VARIETY #1 = PHR03
VARIETY #2 = PHG84

|  | VAR # | BU ACR ABS | BU ACR % MN | YLD SC ABS | MST ABS | EAR SZ ABS | BAR PLT ABS | PLT HT ABS | EAR HT ABS |
|---|---|---|---|---|---|---|---|---|---|
| TOTAL SUM | 1 | 72.8 | 149 | 6.4 | 22.5 | 6.7 | 95.9 | 95.8 | 32.5 |
|  | 2 | 10.2 | 22 | 3.3 | 20.6 | 5.3 | 59.3 | 84.7 | 27.9 |
|  | LOCS | 3 | 3 | 9 | 3 | 6 | 6 | 4 | 4 |
|  | DIFF | 62.6 | 128 | 3.1 | 1.9 | 1.3 | 36.6 | 11.1 | 4.6 |
|  | PROB | .029+ | .002# | .000# | .500 | .121 | .061* | .083* | .285 |

|  | SDG VGR ABS | EST CNT ABS | DRP EAR ABS | TIL LER ABS | GDU SHD ABS | GDU SLK ABS | POL WT ABS | POL WT % MN |
|---|---|---|---|---|---|---|---|---|
| TOTAL SUM | 5.1 | 36.6 | 100.0 | 0.5 | 1607 | 1651 | 252.3 | 145 |
|  | 1.9 | 32.4 | 94.3 | 1.3 | 1680 | 1728 | 175.0 | 101 |
|  | 12 | 33 | 3 | 13 | 30 | 27 | 8 | 8 |
|  | 3.2 | 4.1 | 5.7 | 0.8 | 73 | 77 | 77.3 | 44 |
|  | .000# | .000# | .387 | .059* | .000# | .000# | .009# | .009# |

|  | POL SC ABS | TAS BLS ABS | TAS SZ ABS | TEX EAR ABS | TST WT ABS | GRN APP ABS | SCT GRN ABS | STA GRN |
|---|---|---|---|---|---|---|---|---|
| TOTAL SUM | 7.1 | 7.0 | 6.3 | 6.2 | 56.8 | 6.3 | 5.7 | 6.1 |
|  | 6.0 | 9.0 | 6.0 | 6.4 | 54.5 | 4.7 | 4.3 | 6.2 |
|  | 15 | 3 | 8 | 5 | 3 | 3 | 6 | 8 |
|  | 1.1 | 2.0 | 0.3 | 0.2 | 2.3 | 1.7 | 1.3 | 0.0 |
|  | .012+ | .225 | .563 | .778 | .242 | .214 | .010+ | .916 |

|  | STK LDG | RT LDG | EAR MLD ABS | NLF BLT ABS | STW WLT ABS | ECB 1LF ABS | ECB 2SC ABS |
|---|---|---|---|---|---|---|---|
| TOTAL SUM | 82.6 | 100.0 | 7.0 | 4.5 | 8.0 | 5.2 | 1.0 |
|  | 85.8 | 100.0 | 6.3 | 5.0 | 7.5 | 5.3 | 1.0 |
|  | 3 | 3 | 8 | 2 | 2 | 6 | 3 |
|  | 3.2 | 0.0 | 0.8 | 0.5 | 0.5 | 0.2 | 0.0 |
|  | .813 | 1.00 | .351 | .500 | .500 | .771 | 1.00 |

\* = 10% SIG  
\+ = 5% SIG  
\# = 1% SIG

TABLE 3C

PAIRED INBRED COMPARISON DATA
VARIETY #1 = PHR03
VARIETY #2 = PHM49

|  | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS |
|---|---|---|---|---|---|---|---|---|---|---|---|
| TOTAL SUM | 1 | 60.7 | 125 | 6.6 | 25.8 | 7.1 | 96.2 | 79.1 | 30.6 | 4.9 | 32.3 |
|  | 2 | 58.6 | 124 | 5.7 | 25.7 | 5.6 | 92.2 | 72.8 | 26.9 | 4.1 | 30.3 |
|  | LOCS | 4 | 4 | 33 | 4 | 17 | 12 | 27 | 26 | 43 | 75 |
|  | DIFF | 2.2 | 2 | 0.9 | 0.1 | 1.5 | 4.0 | 6.3 | 3.7 | 0.8 | 2.0 |
|  | PROB | .867 | .950 | .008# | .954 | .000# | .197 | .001# | .006# | .002# | .002# |

|  | DRP EAR | TIL LER | GDU SHD | GDU SLK | POL WT | POL WT | POL SC | TAS BLS | TAS SZ | TEX EAR | TST WT | GRN APP |
|---|---|---|---|---|---|---|---|---|---|---|---|---|

TABLE 3C-continued

PAIRED INBRED COMPARISON DATA
VARIETY #1 = PHR03
VARIETY #2 = PHM49

|  | ABS | ABS | ABS | ABS | ABS | % MNS | ABS | ABS | ABS | ABS | ABS | ABS |
|---|---|---|---|---|---|---|---|---|---|---|---|---|
| TOTAL | 100.0 | 3.4 | 1579 | 1614 | 223.6 | 139 | 6.8 | 7.0 | 6.0 | 7.0 | 54.7 | 6.3 |
| SUM | 98.8 | 8.6 | 1531 | 1557 | 194.0 | 121 | 6.4 | 5.7 | 6.1 | 6.0 | 55.5 | 5.8 |
|  | 3 | 39 | 84 | 77 | 13 | 13 | 38 | 3 | 31 | 10 | 4 | 3 |
|  | 1.2 | 5.1 | 48 | 57 | 29.5 | 17 | 0.4 | 1.3 | 0.1 | 1.0 | 0.8 | 0.5 |
|  | .423 | .082* | .000# | .000# | .032+ | .039+ | .107 | .184 | .752 | .138 | .571 | .622 |
|  | SCT GRN ABS | STA GRN ABS | STK LDG ABS | RT LDG ABS | BRT STK ABS | COM RST ABS | EAR MLD ABS | GLF SPT ABS | HD SMT ABS | MDM CPX ABS | NLF BLT ABS | SLF BLT ABS | STW WLT ABS |
| TOTAL | 6.3 | 5.8 | 70.1 | 100.0 | 100.0 | 6.7 | 6.9 | 4.0 | 92.4 | 3.3 | 5.2 | 4.8 | 6.8 |
| SUM | 6.7 | 6.5 | 64.2 | 97.6 | 100.0 | 5.7 | 5.6 | 3.9 | 92.9 | 3.3 | 4.1 | 3.6 | 6.3 |
|  | 28 | 19 | 5 | 4 | 2 | 3 | 23 | 7 | 1 | 2 | 2 | 14 | 5 |
|  | 0.4 | 0.7 | 5.8 | 2.4 | 0.0 | 1.0 | 1.3 | 0.1 | 0.5 | 0.0 | 1.0 | 1.1 | 0.5 |
|  | .229 | .073* | .469 | .391 | 1.00 | .225 | .005# | .703 |  | .979 | 1.00 | .045+ | .326 |
|  |  |  |  |  |  |  |  |  |  | ECB DPE ABS | ECB 1LF ABS | ECB 2SC ABS |
| TOTAL |  |  |  |  |  |  |  |  |  | 100.0 | 5.2 | 3.9 |
| SUM |  |  |  |  |  |  |  |  |  | 100.0 | 4.5 | 4.6 |
|  |  |  |  |  |  |  |  |  |  | 1 | 30 | 15 |
|  |  |  |  |  |  |  |  |  |  | 0.0 | 0.7 | 0.7 |
|  |  |  |  |  |  |  |  |  |  |  | .005# | .194 |

\* = 10% SIG
\+ = 5% SIG
\# = 1% SIG

TABLE 3D

PAIRED INBRED COMPARISON DATA
VARIETY #1 = PHR03
VARIETY #2 = PHN46

|  | VAR # | BU ACR ABS | BU ACR % MN | YLD SC ABS | MST ABS | EAR SZ ABS | BAR PLT ABS | PLT HT ABS | EAR HT ABS | SDG VGR ABS |
|---|---|---|---|---|---|---|---|---|---|---|
| TOTAL | 1 | 43.4 | 94 | 6.9 | 25.6 | 7.3 | 88.1 | 81.0 | 31.2 | 4.8 |
| SUM | 2 | 55.6 | 141 | 5.8 | 20.6 | 5.2 | 92.8 | 72.7 | 26.5 | 5.5 |
|  | LOCS | 6 | 6 | 24 | 6 | 12 | 12 | 22 | 21 | 42 |
|  | DIFF | 12.2 | 47 | 1.1 | 5.0 | 2.1 | 4.7 | 8.4 | 4.6 | 0.7 |
|  | PROB | .367 | .247 | .003# | .001# | .000# | .081* | .000# | .004# | .001# |
|  | EST CNT ABS | DRP EAR ABS | TIL LER ABS | GDU SHD ABS | GDU SLK ABS | POL WT ABS | POL WT % MNS | POL SC ABS | TAS BLS ABS | TAS SZ ABS |
| TOTAL | 32.7 | 100.0 | 3.4 | 1575 | 1612 | 223.9 | 138 | 7.0 | 8.0 | 6.2 |
| SUM | 32.6 | 100.0 | 1.4 | 1491 | 1504 | 162.2 | 101 | 5.6 | 9.0 | 5.0 |
|  | 68 | 5 | 32 | 68 | 65 | 7 | 7 | 30 | 2 | 23 |
|  | 0.1 | 0.0 | 2.0 | 84 | 108 | 61.7 | 37 | 1.4 | 1.0 | 1.2 |
|  | .896 | 1.00 | .145 | .000# | .000# | .019+ | .028+ | .000# | .500 | .000# |
|  | TEX EAR ABS | TST WT ABS | GRN APP ABS | SCT GRN ABS | STA GRN ABS | STK LDG ABS | RT LDG ABS | BRT STK ABS | COM RST ABS | EAR MLD ABS | GLF SPT ABS | MDM CPX ABS |
| TOTAL | 7.8 | 54.2 | 4.6 | 6.5 | 5.9 | 88.5 | 98.0 | 100.0 | 6.0 | 7.0 | 3.2 | 3.3 |
| SUM | 5.7 | 54.3 | 5.3 | 6.2 | 3.8 | 87.3 | 99.8 | 96.4 | 7.5 | 6.8 | 1.3 | 3.8 |
|  | 6 | 6 | 5 | 21 | 15 | 5 | 5 | 2 | 2 | 16 | 1 | 5 |
|  | 2.2 | 0.1 | 0.7 | 0.3 | 2.2 | 1.2 | 1.8 | 3.6 | 1.5 | 0.2 | 1.9 | 0.5 |
|  | .006# | .925 | .646 | .458 | .000# | .676 | .375 | .500 | .205 | .646 | .012+ | .000# |
|  |  |  |  |  |  |  |  | NLF BLT ABS | SLF BLT ABS | STW WLT ABS | ECB DPE ABS | ECB 1LF ABS | ECB 2SC ABS |
| TOTAL |  |  |  |  |  |  |  | 5.3 | 5.1 | 6.7 | 100.0 | 5.4 | 4.8 |
| SUM |  |  |  |  |  |  |  | 5.3 | 4.1 | 6.3 | 100.0 | 4.4 | 4.3 |
|  |  |  |  |  |  |  |  | 2 | 8 | 1 | 3 | 2 | 23 |
|  |  |  |  |  |  |  |  | 0.1 | 1.0 | 0.3 | 0.0 | 1.0 | 0.6 |
|  |  |  |  |  |  |  |  | .875 | .117 | .742 | 1.00 | .017+ | .162 |

\* = 10% SIG
\+ = 5% SIG
\# = 1% SIG

TABLE 3E

PAIRED INBRED COMPARISON DATA
VARIETY #1 = PHR03
VARIETY #2 = PHR63

| | VAR # | BU ACR ABS | BU ACR % MN | YLD SC ABS | MST ABS | EAR SZ ABS | BAR PLT ABS | PLT HT ABS | EAR HT ABS | SDG VGR ABS |
|---|---|---|---|---|---|---|---|---|---|---|
| TOTAL | 1 | 89.3 | 129 | 6.8 | 23.3 | 7.1 | 98.3 | 79.8 | 28.4 | 4.9 |
| SUM | 2 | 100.5 | 144 | 6.5 | 24.9 | 5.4 | 97.1 | 72.2 | 23.4 | 4.9 |
| | LOCS | 2 | 2 | 28 | 2 | 14 | 11 | 20 | 19 | 32 |
| | DIFF | 11.3 | 15 | 0.3 | 1.6 | 1.6 | 1.3 | 7.7 | 5.0 | 0.0 |
| | PROB | .613 | .629 | .382 | .338 | .000# | .489 | .001# | .003# | .000# |

| | | EST CNT ABS | DRP EAR ABS | TIL LER ABS | GDU SHD ABS | GDU SLK ABS | POL WT ABS | POL WT % MNS | POL SC ABS | TAS BLS ABS | TAS SZ ABS |
|---|---|---|---|---|---|---|---|---|---|---|---|
| TOTAL | | 28.6 | 100.0 | 2.6 | 1573 | 1610 | 262.4 | 152 | 6.7 | 7.0 | 6.0 |
| SUM | | 27.7 | 100.0 | 3.3 | 1460 | 1480 | 219.2 | 126 | 6.7 | 8.0 | 6.2 |
| | | 57 | 1 | 27 | 65 | 62 | 7 | 7 | 29 | 3 | 26 |
| | | 0.9 | 0.0 | 0.7 | 11.3 | 13.0 | 43.2 | 26 | 0.0 | 1.0 | 0.3 |
| | | .063* | | .484 | .000# | .000# | .021+ | .018+ | .905 | .580 | .283 |

| | | TEX EAR ABS | TST WT ABS | GRN APP ABS | SCT GRN ABS | STA GRN ABS | STK LDG ABS | RT LDG ABS | BRT STK ABS | COM RST ABS | EAR MLD ABS |
|---|---|---|---|---|---|---|---|---|---|---|---|
| TOTAL | | 6.8 | 57.5 | 9.0 | 6.5 | 5.7 | 96.6 | 70.8 | 100 | 6.0 | 7.0 |
| SUM | | 7.3 | 57.4 | 8.8 | 7.7 | 4.8 | 97.4 | 67.1 | 99.2 | 8.0 | 7.4 |
| | | 8 | 2 | 2 | 23 | 15 | 1 | 2 | 3 | 1 | 20 |
| | | 0.5 | 0.1 | 0.3 | 1.2 | 0.9 | 0.8 | 3.7 | 0.8 | 2.0 | 0.4 |
| | | .351 | .956 | .500 | .001# | .119 | | .694 | .423 | | .169 |

| | | GLF SPT ABS | MDM CPX ABS | NLF BLT ABS | SLF BLT ABS | STW WLT ABS | ECB 1LF ABS | ECB 2SC ABS |
|---|---|---|---|---|---|---|---|---|
| TOTAL | | 3.5 | 3.3 | 5.7 | 4.7 | 7.3 | 5.1 | 4.9 |
| SUM | | 1.3 | 3.5 | 4.8 | 2.8 | 6.3 | 6.3 | 3.9 |
| | | 4 | 2 | 10 | 3 | 4 | 20 | 7 |
| | | 2.3 | 0.3 | 0.9 | 1.8 | 1.0 | 1.3 | 0.9 |
| | | .014+ | .500 | .064* | .212 | .182 | .001# | .015+ |

\* = 10% SIG
+ = 5% SIG
# = 1% SIG

TABLE 3F

PAIRED INBRED COMPARISON DATA
VARIETY #1 = PHR03
VARIETY #2 = PHV78

| | VAR # | BU ACR ABS | BU ACR % MN | YLD SC ABS | MST ABS | EAR SZ ABS | BAR PLT ABS | PLT HT ABS | EAR HT ABS |
|---|---|---|---|---|---|---|---|---|---|
| TOTAL | 1 | 60.7 | 125 | 6.6 | 25.8 | 6.9 | 95.9 | 78.4 | 30.5 |
| SUM | 2 | 40.1 | 82 | 6.1 | 24.2 | 6.4 | 91.2 | 84.1 | 29.3 |
| | LOCS | 4 | 4 | 30 | 4 | 18 | 11 | 24 | 23 |
| | DIFF | 20.6 | 43 | 0.6 | 1.6 | 0.6 | 4.7 | 5.7 | 1.1 |
| | PROB | .191 | .198 | .019+ | .307 | .037+ | .039+ | .003# | .399 |

| | | SDG VGR ABS | EST CNT ABS | DRP EAR ABS | TIL LER ABS | GDU SHD ABS | GDU SLK ABS | POL WT ABS | POL WT % MNS | POL SC ABS | TAS BLS ABS |
|---|---|---|---|---|---|---|---|---|---|---|---|
| TOTAL | | 5.1 | 30.2 | 100.0 | 3.6 | 1579 | 1614 | 243.1 | 140 | 6.9 | 7.0 |
| SUM | | 4.3 | 25.7 | 99.6 | 2.5 | 1580 | 1623 | 249.4 | 146 | 7.2 | 9.0 |
| | | 45 | 71 | 3 | 34 | 80 | 72 | 9 | 9 | 32 | 3 |
| | | 0.7 | 4.5 | 0.4 | 1.1 | 01 | 08 | 6.3 | 6 | 0.3 | 2.0 |
| | | .009# | .000# | .423 | .481 | .876 | .231 | .843 | .753 | .253 | .225 |

| | | TAS SZ ABS | TEX EAR ABS | TST WT ABS | GRN APP ABS | SCT GRN ABS | STA GRN ABS | STK LDG ABS | RT LDG ABS | BRT STK ABS | COM SMT ABS |
|---|---|---|---|---|---|---|---|---|---|---|---|
| TOTAL | | 6.2 | 7.0 | 54.7 | 6.3 | 6.3 | 5.5 | 70.1 | 90.6 | 100.0 | 6.7 |
| SUM | | 7.1 | 3.2 | 51.0 | 4.5 | 5.6 | 5.8 | 83.6 | 77.9 | 100.0 | 6.3 |
| | | 29 | 11 | 4 | 3 | 26 | 21 | 5 | 6 | 2 | 3 |
| | | 0.9 | 3.8 | 3.8 | 1.8 | 0.7 | 0.3 | 13.5 | 12.6 | 0.0 | 0.3 |
| | | .000# | .000# | .038+ | .053* | .018+ | .421 | .033+ | .062* | 1.00 | .742 |

| | | EAR MLD ABS | GLF SPT ABS | HD SMT ABS | MDM CPX ABS | NLF BLT ABS | SLF BLT ABS | STW WLT ABS | ECB DPE ABS | ECB 1LF ABS | ECB 2SC ABS |
|---|---|---|---|---|---|---|---|---|---|---|---|
| TOTAL | | 7.1 | 4.1 | 84.8 | 3.4 | 4.9 | 4.9 | 6.8 | 98.9 | 5.1 | 3.7 |
| SUM | | 5.5 | 3.2 | 97.5 | 2.9 | 5.2 | 4.0 | 6.4 | 92.2 | 5.8 | 3.7 |
| | | 20 | 22 | 8 | 5 | 17 | 15 | 5 | 3 | 33 | 19 |

TABLE 3F-continued

PAIRED INBRED COMPARISON DATA
VARIETY #1 = PHR03
VARIETY #2 = PHV78

| 1.6 | 0.9 | 12.7 | 0.5 | 0.3 | 1.0 | 0.4 | 6.7 | 0.8 | 0.0 |
|---|---|---|---|---|---|---|---|---|---|
| .001# | .002# | .031+ | .089* | .487 | .001# | .477 | .225 | .003# | .946 |

* = 10% SIG
+ = 5% SIG
# = 1% SIG

TABLE 4A

AVERAGE INBRED BY TESTER PERFORMANCE COMPARING PHR03 TO PHJ90 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| TOTAL | REPLIC. | 172 | 171 | 171 | 171 | 172 | 43 | 157 | 57 |
|---|---|---|---|---|---|---|---|---|---|
| MEAN WTS | PHR03 | 124 | 106 | 158 | 105 | 108 | 104 | 102 | 102 |
| MEAN WTS | PHJ90 | 119 | 101 | 151 | 101 | 99 | 97 | 98 | 102 |
|  | DIFF. | 5 | 5 | 6 | 4 | 9 | 9 | 7 | 4 |
|  | INBRED | PRM | SEL IND | BU ACR | YLD | MST | GDU SHD | STK LDG | RT LDG |

| TOTAL | 99 | 172 | 83 | 68 | 120 | 179 | 75 | 75 | 113 | 16 |
|---|---|---|---|---|---|---|---|---|---|---|
| MEAN WTS | 113 | 103 | 112 | 101 | 100 | 100 | 105 | 102 | 100 | 102 |
| MEAN WTS | 74 | 101 | 101 | 99 | 100 | 100 | 93 | 88 | 100 | 99 |
|  | 0 | 39 | 2 | 11 | 2 | 0 | 1 | 12 | 14 | 0 |
|  | STA GRN | TST WTA | GRN APP | SDG VGR | EST CNT | STK CNT | PLT HT | EAR HT | DRP EAR | BRT STK |

TABLE 4B

AVERAGE INBRED BY TESTER PERFORMANCE COMPARING PHR03 TO PHK56 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| TOTAL | REPLIC. | 10 | 10 | 10 | 10 | 10 | 3 | 10 | 4 |
|---|---|---|---|---|---|---|---|---|---|
| MEAN WTS | PHR03 | 121 | 105 | 140 | 107 | 109 | 101 | 100 | 101 |
| MEAN WTS | PHK56 | 113 | 93 | 124 | 95 | 90 | 95 | 97 | 106 |
|  | DIFF. | 8 | 12 | 16 | 11 | 19 | 6 | 3 | 6 |
|  | INBRED | PRM | SEL IND | BU ACR | YLD | MST | GDU SHD | STK LDG | RT LDG |

| TOTAL | 6 | 10 | 6 | 5 | 5 | 10 | 5 | 5 | 6 |
|---|---|---|---|---|---|---|---|---|---|
| MEAN WTS | 94 | 101 | 102 | 110 | 104 | 101 | 103 | 96 | 101 |
| MEAN WTS | 61 | 100 | 98 | 96 | 102 | 100 | 100 | 91 | 100 |
|  | 33 | 1 | 4 | 13 | 2 | 1 | 2 | 4 | 1 |
|  | STA GRN | TST WTA | GRN APP | SDG VGR | EST CNT | STK CNT | PLT HT | EAR HT | DRP EAR |

TABLE 4C

AVERAGE INBRED BY TESTER PERFORMANCE COMPARING PHR03 TO PHM49 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| TOTAL | REPLIC. | 101 | 114 | 114 | 114 | 115 | 30 | 109 | 49 |
|---|---|---|---|---|---|---|---|---|---|
| MEAN WTS | PHR03 | 121 | 107 | 171 | 106 | 101 | 104 | 98 | 99 |
| MEAN WTS | PHM49 | 121 | 91 | 151 | 94 | 98 | 102 | 101 | 99 |
|  | DIFF. | 1 | 17 | 20 | 12 | 3 | 2 | 3 | 1 |
|  | INBRED | PRM | SEL IND | BU ACR | YLD | MST | GDU SHD | STK LDG | RT LDG |

| TOTAL | 66 | 113 | 28 | 61 | 86 | 118 | 58 | 62 | 51 | 16 |
|---|---|---|---|---|---|---|---|---|---|---|
| MEAN WTS | 93 | 102 | 103 | 102 | 102 | 101 | 108 | 110 | 100 | 105 |
| MEAN WTS | 112 | 100 | 97 | 83 | 91 | 97 | 101 | 101 | 100 | 101 |
|  | 19 | 2 | 6 | 19 | 11 | 5 | 7 | 9 | 0 | 3 |
|  | STA GRN | TST WTA | GRN APP | SDG VGR | EST CNT | STK CNT | PLT HT | EAR HT | DRP EAR | BRT STK |

TABLE 4D

AVERAGE INBRED BY TESTER PERFORMANCE COMPARING PHR03 TO PHN46 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| TOTAL | REPLIC. | 608 | 653 | 653 | 653 | 656 | 177 | 628 | 161 |
|---|---|---|---|---|---|---|---|---|---|
| MEAN WTS | PHR03 | 123 | 107 | 160 | 106 | 104 | 103 | 100 | 100 |
| MEAN WTS | PHN46 | 121 | 104 | 156 | 103 | 101 | 101 | 101 | 102 |
|  | DIFF. | 2 | 3 | 5 | 3 | 3 | 2 | 1 | 1 |
|  | INBRED | PRM | SEL IND | BU ACR | YLD | MST | GDU SHD | STK LDG | RT LDG |

| TOTAL | 400 | 652 | 395 | 346 | 486 | 689 | 362 | 362 | 316 | 45 |
|---|---|---|---|---|---|---|---|---|---|---|
| MEAN WTS | 106 | 103 | 108 | 102 | 100 | 100 | 104 | 101 | 100 | 102 |
| MEAN WTS | 120 | 99 | 94 | 112 | 103 | 101 | 97 | 99 | 100 | 91 |
|  | 14 | 4 | 14 | 10 | 3 | 1 | 7 | 2 | 0 | 11 |
|  | STA GRN | TST WTA | GRN APP | SDG VGR | EST CNT | STK CNT | PLT HT | EAR HT | DRP EAR | BRT STK |

TABLE 4E

AVERAGE INBRED BY TESTER PERFORMANCE COMPARING PHR03 TO PHR55 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| TOTAL | REPLIC. | 259 | 270 | 270 | 270 | 271 | 62 | 249 | 107 | 155 |
|---|---|---|---|---|---|---|---|---|---|---|
| MEAN WTS | PHR03 | 124 | 107 | 162 | 106 | 104 | 102 | 100 | 102 | 101 |
| MEAN WTS | PHR55 | 126 | 101 | 156 | 102 | 106 | 101 | 99 | 104 | 98 |
|  | DIFF. | 1 | 6 | 6 | 4 | 3 | 1 | 1 | 2 | 3 |
|  | INBRED | PRM | SEL IND | BU ACR | YLD | MST | GDU SHD | STK LDG | RT LDG | STA GRN |

| TOTAL | REPLIC. | 271 | 76 | 129 | 196 | 290 | 132 | 132 | 128 | 56 |
|---|---|---|---|---|---|---|---|---|---|---|
| MEAN WTS | PHR03 | 103 | 109 | 102 | 100 | 100 | 103 | 100 | 100 | 103 |
| MEAN WTS | PHR55 | 101 | 108 | 103 | 101 | 100 | 100 | 98 | 100 | 97 |
|  | DIFF. | 2 | 1 | 1 | 1 | 1 | 3 | 2 | 0 | 5 |
|  | INBRED | TST WTA | GRN APP | SDG VGR | EST CNT | STK CNT | PLT HT | EAR HT | DRP EAR | BRT STK |

TABLE 4F

AVERAGE INBRED BY TESTER PERFORMANCE COMPARING PHR03 TO PHR63 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| TOTAL | REPLIC. | 77 | 76 | 76 | 76 | 77 | 20 | 73 | 43 | 37 |
|---|---|---|---|---|---|---|---|---|---|---|
| MEAN WTS | PHR03 | 123 | 109 | 164 | 106 | 100 | 101 | 101 | 95 | 92 |
| MEAN WTS | PHR63 | 126 | 100 | 156 | 101 | 106 | 97 | 98 | 100 | 78 |
|  | DIFF. | 3 | 8 | 8 | 5 | 6 | 3 | 3 | 5 | 14 |
|  | INBRED | PRM | SEL IND | BU ACR | YLD | MST | GDU SHD | STK LDG | RT LDG | STA GRN |

| TOTAL | REPLIC. | 77 | 14 | 36 | 56 | 83 | 38 | 38 | 36 | 14 |
|---|---|---|---|---|---|---|---|---|---|---|
| MEAN WTS | PHR03 | 102 | 110 | 94 | 101 | 101 | 101 | 100 | 100 | 104 |
| MEAN WTS | PHR63 | 101 | 103 | 105 | 99 | 99 | 98 | 99 | 100 | 102 |
|  | DIFF. | 1 | 7 | 11 | 2 | 1 | 3 | 1 | 0 | 2 |
|  | INBRED | TST WTA | GRN APP | SDG VGR | EST CNT | STK CNT | PLT HT | EAR HT | DRP EAR | BRT STK |

TABLE 4G

AVERAGE INBRED BY TESTER PERFORMANCE COMPARING PHR03 TO PHT22 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| TOTAL | REPLIC. | 6 | 6 | 6 | 6 | 6 | 6 | 4 | 4 | 6 | 6 | 2 | 2 | 4 |
|---|---|---|---|---|---|---|---|---|---|---|---|---|---|---|
| MEAN WTS | PHR03 | 127 | 113 | 203 | 110 | 103 | 97 | 109 | 93 | 103 | 105 | 105 | 100 | 106 |
| MEAN WTS | PHT22 | 126 | 94 | 177 | 96 | 99 | 101 | 88 | 77 | 101 | 100 | 104 | 108 | 106 |
|  | DIFF. | 1 | 19 | 26 | 14 | 3 | 5 | 20 | 15 | 2 | 5 | 2 | 7 | 0 |
|  | INBRED | PRM | SEL IND | BU ACR | YLD | MST | STK LDG | RT LDG | STA GRN | TST WTA | STK CNT | PLT HT | EAR HT | BRT STK |

TABLE 5

PHR03 HYBRID COMPARED TO PIONEER HYBRID 3503
VARIETY #1 = PHR03 HYBRID
VARIETY #2 = 3503

| YEAR | VAR # | BU ACR ABS | BU ACR % MN | MST ABS | PLT HT ABS | EAR HT ABS | SDG VGR ABS | EST CNT ABS |
|---|---|---|---|---|---|---|---|---|
| TOTAL SUM | 1 | 153.5 | 105 | 21.9 | 105.5 | 46.4 | 6.0 | 58.1 |
| | 2 | 144.3 | 99 | 20.0 | 93.1 | 42.8 | 6.1 | 57.2 |
| | LOCS | 137 | 137 | 137 | 70 | 70 | 70 | 99 |
| | DIFF | 9.2 | 6 | 1.9 | 12.4 | 3.6 | 0.1 | 0.9 |
| | PROB | .000# | .000# | .000# | .000# | .000# | .295 | .029+ |

| YEAR | VAR # | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 99.7 | 1456 | 58.7 | 7.9 | 6.0 | 94.3 | 93.6 | 96.9 |
| | 2 | 99.7 | 1360 | 58.9 | 7.4 | 4.4 | 90.3 | 98.7 | 97.2 |
| | LOCS | 82 | 40 | 135 | 100 | 73 | 135 | 38 | 4 |
| | DIFF | 0.0 | 96 | 0.2 | 0.4 | 1.7 | 4.0 | 5.1 | 0.4 |
| | PROB | .958 | .000# | .011+ | .000# | .000# | .000# | .010+ | .818 |

\* = 10% SIG
+ = 5% SIG
# = 1% SIG

TABLE 6

PHR03 HYBRID COMPARED TO PIONEER HYBRID 3417
VARIETY #1-PHR03 HYBRID
VARIETY #2-3417

| YEAR | VAR # | BU ACR ABS | BU ACR % MN | MST ABS | PLT HT ABS | EAR HT ABS | SDG VGR ABS | EST CNT ABS | DRP EAR ABS |
|---|---|---|---|---|---|---|---|---|---|
| TOTAL SUM | 1 | 156.9 | 106 | 21.1 | 106.5 | 44.8 | 6.2 | 58.1 | 99.7 |
| | 2 | 144.0 | 97 | 18.8 | 97.1 | 37.9 | 6.0 | 58.6 | 99.7 |
| | LOCS | 241 | 241 | 242 | 126 | 126 | 115 | 161 | 111 |
| | DIFF | 12.9 | 8 | 2.3 | 9.4 | 6.9 | 0.2 | 0.5 | 0.0 |
| | PROB | .000# | .000# | .000# | .000# | .000# | .018+ | .093* | .921 |

| | VAR # | GDU SHD ABS | TST WTA ABS | GRN APP ABS | STA GRN ABS | STK LDG ABS | RT LDG ABS | BRT STK ABS |
|---|---|---|---|---|---|---|---|---|
| TOTAL SUM | 1 | 1463 | 59.1 | 8.1 | 5.7 | 94.7 | 94.7 | 97.8 |
| | 2 | 1379 | 57.2 | 7.1 | 4.2 | 91.6 | 97.9 | 94.3 |
| | LOCS | 56 | 239 | 158 | 139 | 234 | 55 | 12 |
| | DIFF | 84 | 1.9 | 1.0 | 1.5 | 3.0 | 3.2 | 3.5 |
| | PROB | .000# | .000# | .000# | .000# | .000# | .028+ | .329 |

\* = 10% SIG
+ = 5% SIG
# = 1% SIG

TABLE 7

PHR03 HYBRID COMPARED TO PIONEER HYBRID 3398
VARIETY #1-PHR03 HYBRID
VARIETY #2-3398

| YEAR | VAR # | BU ACR ABS | BU ACR % MN | MST ABS | PLT HT ABS | EAR HT ABS | SDG VGR ABS | EST CNT ABS |
|---|---|---|---|---|---|---|---|---|
| TOTAL SUM | 1 | 160.5 | 105 | 22.6 | 106.1 | 44.3 | 6.1 | 57.9 |
| | 2 | 153.2 | 101 | 20.7 | 93.7 | 38.5 | 6.0 | 58.0 |
| | LOCS | 79 | 79 | 80 | 34 | 34 | 32 | 54 |
| | DIFF | 7.3 | 4 | 1.9 | 12.4 | 5.8 | 0.1 | 0.1 |
| | PROB | .002# | .019+ | .000# | .000# | .000# | .710 | .766 |

| YEAR | VAR # | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 99.8 | 1463 | 58.7 | 7.9 | 6.0 | 94.4 | 98.4 | 97.7 |
| | 2 | 99.8 | 1370 | 57.4 | 7.1 | 3.9 | 91.0 | 98.3 | 94.7 |
| | LOCS | 55 | 19 | 80 | 39 | 45 | 74 | 27 | 7 |
| | DIFF | 0.0 | 93 | 1.3 | 0.8 | 2.1 | 3.3 | 0.2 | 3.0 |
| | PROB | .891 | .000# | .000# | .000# | .000# | .023+ | .825 | .383 |

TABLE 8

PHR03 HYBRID COMPARED TO PIONEER HYBRID 3317
VARIETY #1 = PHR03 HYBRID
VARIETY #2 = 3317

| YEAR | VAR # | BU ACR ABS | BU ACR % MN | MST ABS | PLT HT ABS | EAR HT ABS | SDG VGR ABS | EST CNT ABS |
|---|---|---|---|---|---|---|---|---|
| TOTAL SUM | 1 | 159.1 | 106 | 21.6 | 107.2 | 45.1 | 6.2 | 57.6 |
|  | 2 | 154.8 | 103 | 21.1 | 99.9 | 44.5 | 6.7 | 59.8 |
|  | LOCS | 270 | 270 | 271 | 140 | 140 | 137 | 198 |
|  | DIFF | 4.3 | 3 | 0.4 | 7.3 | 0.6 | 0.6 | 2.1 |
|  | PROB | .000# | .001# | .000# | .000# | .066* | .000# | .000# |

| | VAR # | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 99.8 | 1457 | 58.8 | 7.9 | 5.5 | 93.6 | 95.6 | 98.3 |
|  | 2 | 99.9 | 1433 | 56.6 | 6.7 | 6.2 | 94.4 | 97.9 | 87.0 |
|  | LOCS | 132 | 70 | 269 | 175 | 155 | 259 | 70 | 18 |
|  | DIFF | 0.1 | 24 | 2.2 | 1.2 | 0.7 | 0.8 | 2.3 | 11.3 |
|  | PROB | .274 | .000# | .000# | .000# | .000# | .083* | .046+ | .031+ |

\* = 10% SIG
+ = 5% SIG
# = 1% SIG

TABLE 9

PHR03 HYBRID COMPARED TO PIONEER HYBRID 3189
VARIETY #1-PHR03 HYBRID
VARIETY #2-3189

| YEAR | VAR # | BU ACR ABS | BU ACR % MN | MST ABS | BAR PLT ABS | PLT HT ABS | EAR HT ABS | SDG VGR ABS | EST CNT ABS |
|---|---|---|---|---|---|---|---|---|---|
| TOTAL SUM | 1 | 161.9 | 106 | 20.8 | 91.1 | 109.0 | 45.1 | 6.3 | 57.9 |
|  | 2 | 146.2 | 96 | 21.9 | 68.5 | 101.3 | 42.8 | 5.0 | 55.2 |
|  | LOCS | 252 | 252 | 252 | 1 | 130 | 130 | 137 | 183 |
|  | DIFF | 15.7 | 10 | 1.1 | 22.6 | 7.7 | 2.3 | 1.3 | 2.7 |
|  | PROB | .000# | .000# | .000# |  | .000# | .000# | .000# | .000# |

| YEAR | VAR # | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 99.7 | 1448 | 59.0 | 7.8 | 5.3 | 94.1 | 93.3 | 98.2 |
|  | 2 | 99.8 | 1428 | 57.9 | 7.3 | 6.3 | 96.0 | 94.4 | 92.3 |
|  | LOCS | 112 | 74 | 250 | 136 | 151 | 228 | 80 | 27 |
|  | DIFF | 0.1 | 19 | 1.1 | 0.6 | 1.0 | 1.9 | 1.0 | 5.9 |
|  | PROB | .394 | .000# | .000# | .000# | .000# | .000# | .516 | .034+ |

\* = 10% SIG
+ = 5% SIG
# = 1% SIG

TABLE 10

PHR03 HYBRID COMPARED TO PIONEER HYBRID 3180
VARIETY #1-PHR03 HYBRID
VARIETY #2-3180

| YEAR | VAR # | BU ACR ABS | BU ACR % MN | MST ABS | BAR PLT ABS | PLT HT ABS | EAR HT ABS | SDG VGR ABS | EST CNT ABS |
|---|---|---|---|---|---|---|---|---|---|
| TOTAL SUM | 1 | 162.4 | 106 | 21.0 | 93.8 | 109.1 | 45.2 | 6.3 | 57.1 |
|  | 2 | 153.2 | 100 | 21.4 | 78.8 | 107.6 | 45.3 | 6.1 | 55.5 |
|  | LOCS | 413 | 413 | 418 | 4 | 201 | 211 | 185 | 253 |
|  | DIFF | 9.2 | 6 | 0.5 | 15.0 | 1.5 | 0.1 | 0.2 | 1.6 |
|  | PROB | .000# | .000# | .000# | .135 | .000# | .814 | .042+ | .000# |

| YEAR | VAR # | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 99.8 | 1441 | 58.7 | 8.0 | 5.2 | 93.3 | 94.4 | 98.3 |
|  | 2 | 99.8 | 1440 | 56.2 | 6.7 | 5.3 | 92.8 | 91.3 | 93.4 |
|  | LOCS | 151 | 92 | 412 | 213 | 241 | 367 | 107 | 29 |
|  | DIFF | 0.1 | 01 | 2.5 | 1.2 | 0.1 | 0.5 | 3.1 | 4.8 |
|  | PROB | .109 | .855 | .000# | .000# | .370 | .203 | .030+ | .006# |

TABLE 11
PHR03 HYBRID COMPARED TO PIONEER HYBRID 3162
VARIETY #1-PHR03 HYBRID
VARIETY #2-3162

| YEAR | VAR # | BU ACR ABS | BU ACR % MN | MST ABS | PLT HT ABS | EAR HT ABS | SDG VGR ABS | EST CNT ABS |
|---|---|---|---|---|---|---|---|---|
| TOTAL SUM | 1 | 163.5 | 106 | 19.8 | 105.9 | 43.9 | 6.1 | 59.4 |
|  | 2 | 160.9 | 104 | 21.5 | 99.5 | 41.7 | 6.6 | 60.1 |
|  | LOCS | 146 | 146 | 146 | 74 | 74 | 73 | 100 |
|  | DIFF | 2.6 | .2 | 1.7 | 6.4 | 2.2 | 0.4 | 0.7 |
|  | PROB | .110 | .092* | .000# | .000# | .000# | .002# | .077* |

| YEAR | VAR # | DRP EAR ABS | GDU SHD ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 99.7 | 1448 | 59.6 | 8.4 | 5.0 | 95.1 | 95.6 | 98.1 |
|  | 2 | 99.9 | 1401 | 58.6 | 8.2 | 4.8 | 93.9 | 96.7 | 96.0 |
|  | LOCS | 63 | 36 | 144 | 34 | 83 | 132 | 57 | 26 |
|  | DIFF | 0.2 | 48 | 0.9 | 0.1 | 0.2 | 1.2 | 1.1 | 2.1 |
|  | PROB | .091* | .000# | .000# | .231 | .207 | .041+ | .320 | .083* |

\* = 10% SIG
+ = 5% SIG
# = 1% SIG

TABLE 12
PHR03 HYBRID COMPARED TO PIONEER HYBRID 3159
VARIETY #1-PHR03 HYBRID
VARIETY #2-3159

| YEAR | VAR # | BU ACR ABS | BU ACR % MN | MST ABS | PLT HT ABS | EAR HT ABS | SDG VGR ABS | EST CNT ABS |
|---|---|---|---|---|---|---|---|---|
| TOTAL SUM | 1 | 167.2 | 107 | 18.3 | 106.1 | 41.8 | 6.2 | 60.9 |
|  | 2 | 154.1 | 98 | 19.5 | 99.8 | 40.7 | 5.5 | 59.8 |
|  | LOCS | 61 | 61 | 62 | 26 | 26 | 36 | 50 |
|  | DIFF | 13.1 | 9 | 1.1 | 6.4 | 1.1 | 0.7 | 1.1 |
|  | PROB | .000# | .000# | .000# | .000# | .057* | .000# | .061* |

| YEAR | VAR # | DRP EAR ABS | GDU SHD ABS | TST WTA ABS | STA GRN ABS | STK LDG ABS | RT LDG ABS | BRT STK ABS |
|---|---|---|---|---|---|---|---|---|
| TOTAL SUM | 1 | 99.7 | 1426 | 60.5 | 4.7 | 96.0 | 95.9 | 98.5 |
|  | 2 | 99.8 | 1383 | 59.3 | 5.5 | 95.0 | 96.0 | 94.3 |
|  | LOCS | 14 | 12 | 62 | 40 | 57 | 21 | 16 |
|  | DIFF | 0.1 | 43 | 1.2 | 0.8 | 0.9 | 0.2 | 4.2 |
|  | PROB | .346 | .002# | .000# | .011+ | .433 | .903 | .049+ |

\* = 10% SIG
+ = 5% SIG
# = 1% SIG

Deposits

Applicants have made available to the public without restriction a deposit of at least 2500 seeds of Inbred Corn Line PHR03 with the American Type Culture Collection (ATCC), Rockville, Md. 20852 USA, ATCC Deposit No. 97034. The seeds deposited with the ATCC are taken from the same deposit maintained by Pioneer Hi-Bred International, Inc., 700 Capital Square, 400 Locust Street, Des Moines, Iowa 50309 since prior to the filing date of this application. This deposit of the Inbred Corn Line PHR03 will be maintained without restriction in the ATCC depository, which is a public depository, for a period of 30 years, or 5 years after the most recent request, or for the effective life of the patent, whichever is longer, and will be replaced if it becomes nonviable during that period.

What is claimed is:

1. Inbred corn seed designated PHR03 and having ATCC Accession No. 97034.

2. A corn plant and its plant parts produced by the seed of claim 1.

3. An inbred corn plant having a genotype capable of expressing all the physiological and morphological characteristics of PHR03 having ATCC accession number 97034.

4. A corn plant regenerated from the cells or protoplasts of a culture of tissue selected from the group consisting of meristemetic tissue, immature embryos, microspores and pollen taken from a plant according to claim 2 and having a genotype capable of expressing all the physiological and morphological characteristics of inbred corn plant PHR03 having ATCC accession number 97034.

5. A method of producing hybrid corn having the characteristics of high yield and good grain appearance with below average root lodging across a wide geographic region when compared to similarly adapted hybrids comprising the steps of:
    (a) planting in pollinating proximity seeds of corn inbred lines PHR03 having ATCC accession number 97034 and another inbred line;
    (b) cultivating corn plants resulting from said planting until the time the plants bear flowers;
    (c) emasculating the flowers of the plants of either inbred line;
    (d) allowing natural cross pollinating to occur between said inbred lines; and
    (e) harvesting seeds produced on said emasculated plants of the inbred line.

6. $F_1$ hybrid corn seed and plants therefrom produced by crossing inbred corn plant PHR03 having ATCC accession number 97034 with another corn plant that is not PHR03.

* * * * *